United States Patent
Chen et al.

(10) Patent No.: US 6,908,597 B2
(45) Date of Patent: Jun. 21, 2005

(54) AIR SANITIZING DEVICE FOR VEHICLES

(76) Inventors: Chug-Ming Chen, 1st Floor, No. 5, Lane 284, Yong Ping Rd., Yong Ho, Taipei (TW); Chen-Chen Liu, 1st Floor, No. 5, Lane 284, Yong Ping Rd., Yong Ho, Taipei (TW)

(*) Notice: Subject to any disclaimer, the term of this patent is extended or adjusted under 35 U.S.C. 154(b) by 562 days.

(21) Appl. No.: 10/050,474

(22) Filed: Jan. 15, 2002

(65) Prior Publication Data

US 2003/0133859 A1 Jul. 17, 2003

(51) Int. Cl.[7] .............. A61L 9/00; A61L 2/00; A62B 7/08; B01J 19/08
(52) U.S. Cl. ............. 422/305; 422/1; 422/24; 422/124; 422/186.3; 422/300; 422/306; 422/900
(58) Field of Search ............... 422/1, 4–5, 24, 422/121, 124, 186, 186.3, 300, 305, 306, 900

(56) References Cited

U.S. PATENT DOCUMENTS

| 5,334,347 A | * | 8/1994 | Hollander ............ 422/24 |
| 5,660,719 A | * | 8/1997 | Kurtz et al. ............ 210/85 |
| 5,681,374 A | * | 10/1997 | Von Glehn ............ 96/16 |
| 5,961,920 A | * | 10/1999 | Soremark ............ 422/24 |
| 2002/0098109 A1 | * | 7/2002 | Nelson et al. |

* cited by examiner

Primary Examiner—Robert J. Warden, Sr.
Assistant Examiner—Monzer R. Chorbaji
(74) Attorney, Agent, or Firm—Charles E. Baxley

(57) ABSTRACT

An air sanitizing device for vehicles includes a casing attached to an air vent of the vehicle and having a passage defined therethrough. An ultraviolet LCD is located in the passage and powered by a power supply device connected to the casing. The power supply device can be powered by batteries, AC or DC electric current.

8 Claims, 8 Drawing Sheets

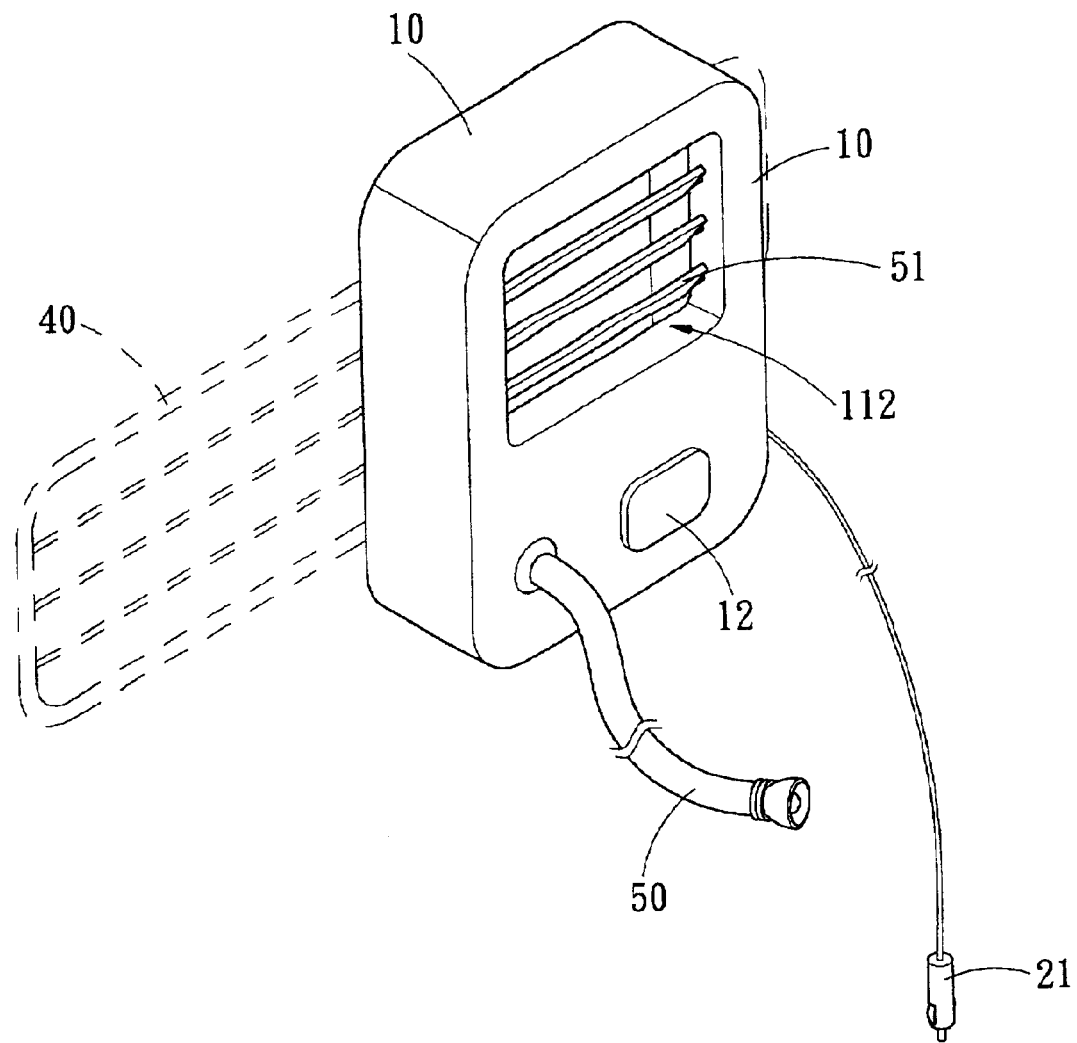
F I G. 3

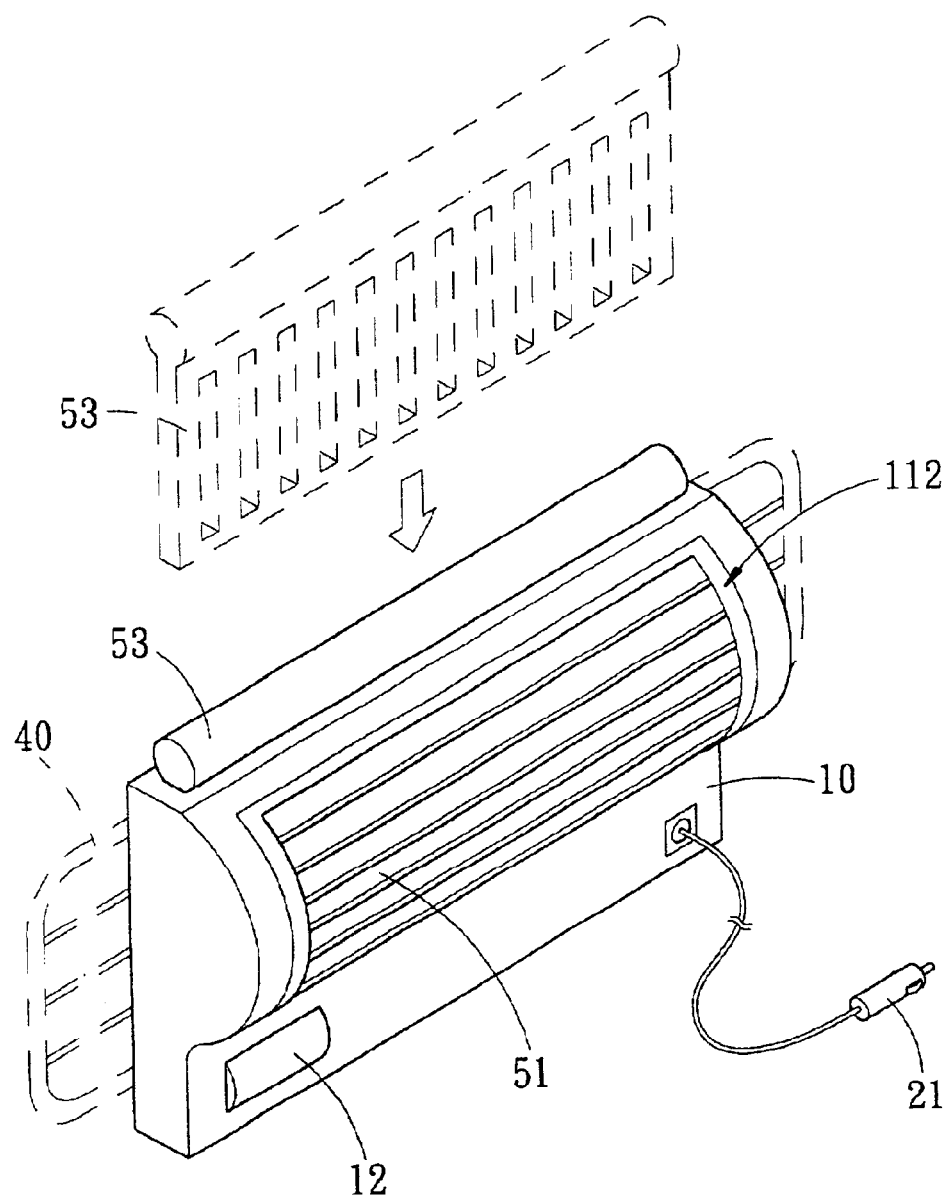
F I G. 5

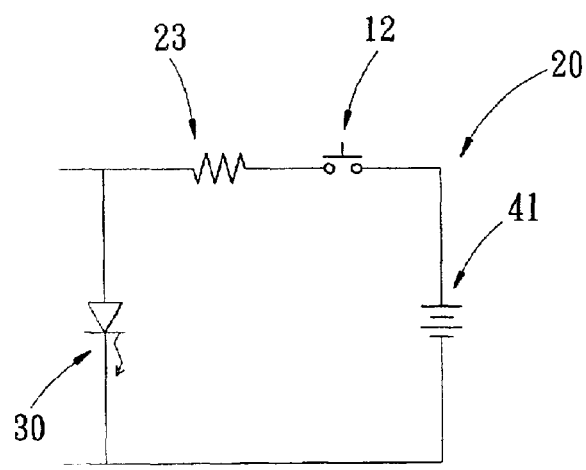
F I G. 7
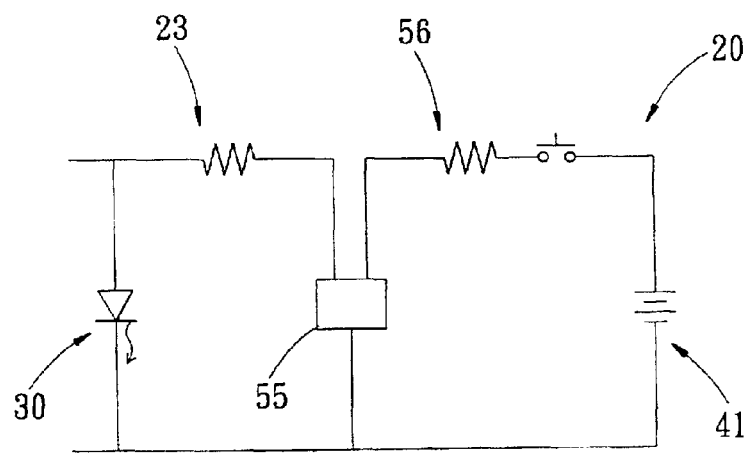
F I G. 8

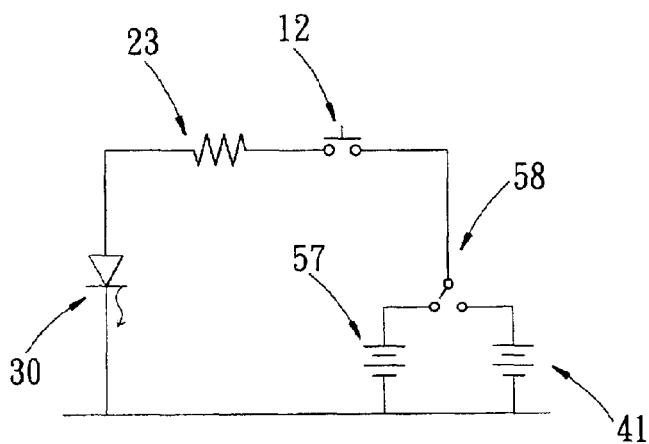
F I G. 9
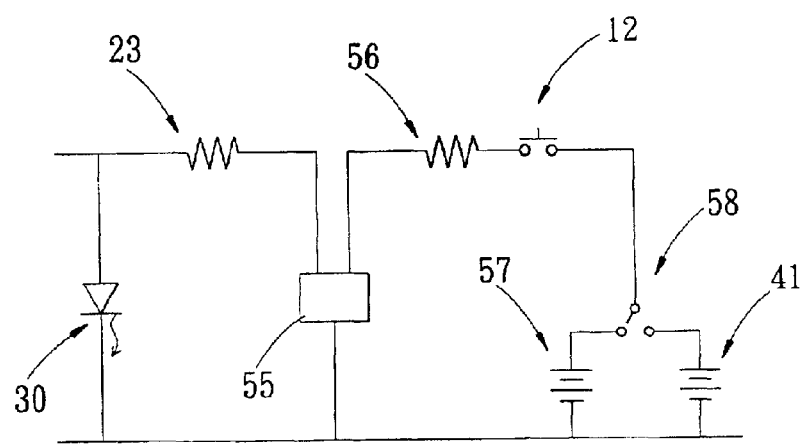
F I G. 10

AIR SANITIZING DEVICE FOR VEHICLES

FIELD OF THE INVENTION

The present invention relates to a sanitizing device having ultraviolet LCD and attached to an air outlet of the air vent to purify the air sent in the vehicles.

BACKGROUND OF THE INVENTION

A vehicle generally has several air vents located at the dashboard so as to send air into the interior of the vehicle. The air quality of big cities is so bad that the drivers usually close the windows of their vehicles while driving so as to reduce the bad air entering into the vehicles. A simple filtering member such as a netted plate may be used to roughly filter the air coming from the air vents, it is not satisfied for the passengers in the vehicles because there are varieties types of germs in the air and are harmful to the passengers' health.

SUMMARY OF THE INVENTION

The present invention relates to an air sanitizing device for vehicles and the device comprises a casing attached to an air vent of the vehicle and having a passage including an inlet and an outlet. An ultraviolet LCD is located in the passage and powered by a power supply device connected to the casing.

The primary object of the present invention is to provide an air sanitizing device that is attached to the air vent and able to kill the germs in the air.

The present invention will become more obvious from the following description when taken in connection with the accompanying drawings which show, for purposes of illustration only, a preferred embodiment in accordance with the present invention.

BRIEF DESCRIPTION OF THE DRAWINGS

FIG. 3 shows another embodiment of the air sanitizing device of the present invention;

FIG. 5 is an exploded view to show the air sanitizing device of the present invention and an ozone generating device;

FIGS. 7 to 10 respectively show the electric circuits used in the air sanitizing device of the present invention.

DETAILED DESCRIPTION OF THE PREFERRED EMBODIMENTS

Figure 1:
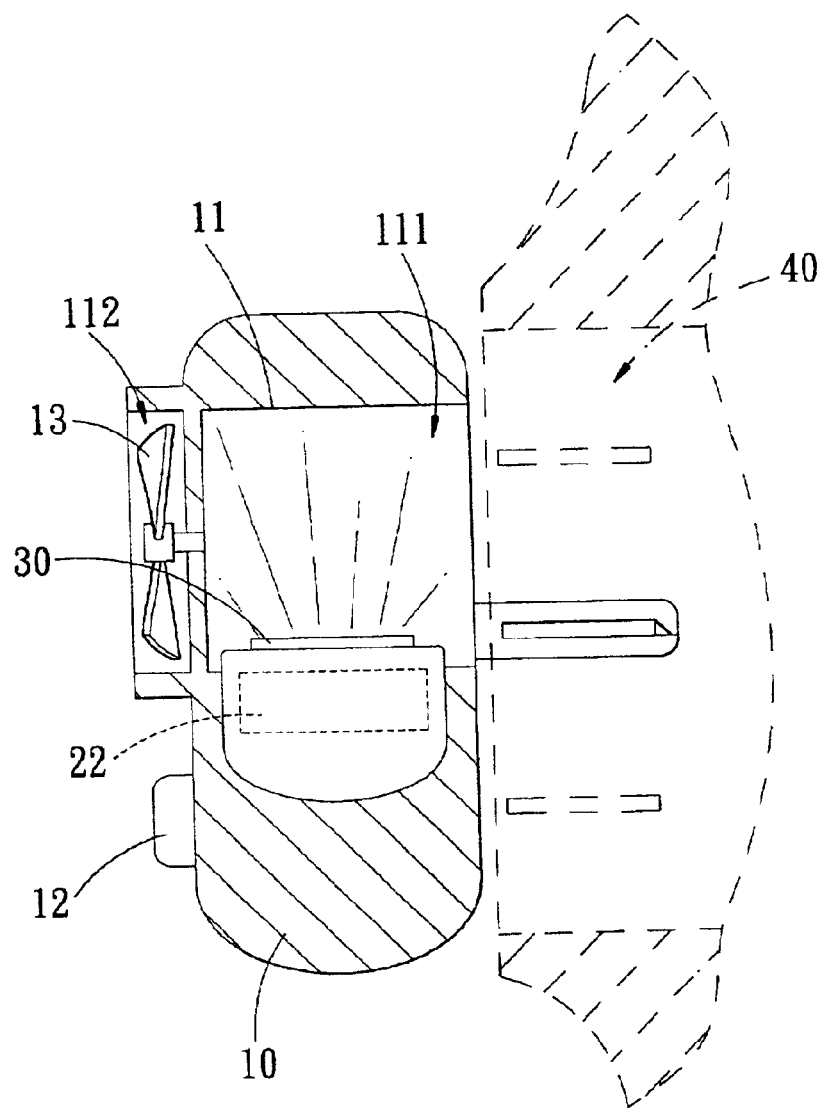
FIG. 1 is a cross sectional view to show the air sanitizing device of the present invention attached to an air vent of vehicles.
Figure 2:
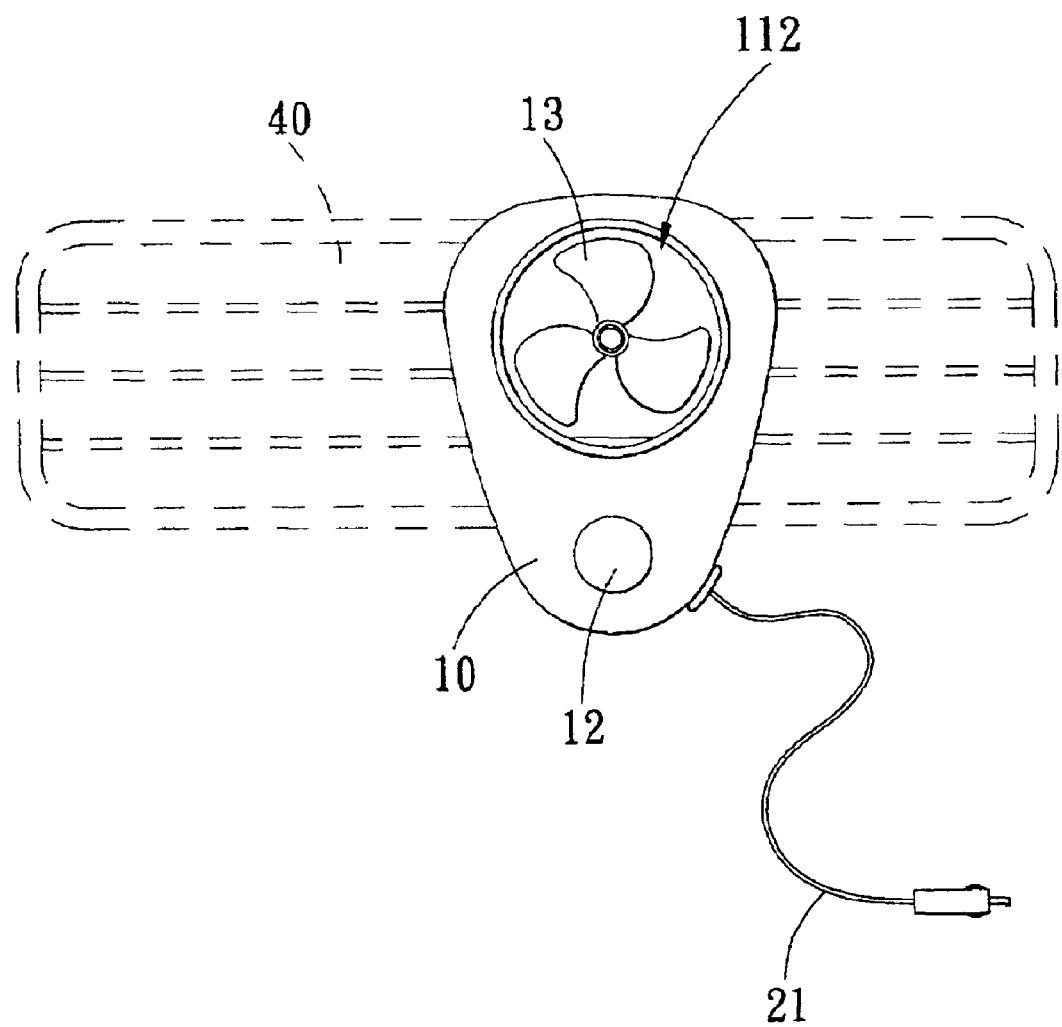
FIG. 2 is a front view to show the air sanitizing device of the present invention attached to an air vent of vehicles.

Referring to FIGS. 1 and 2, the air sanitizing device for vehicles of the present invention comprises a casing 10 which is attached to an air vent 40 of the vehicle by known ways, and a passage 11 is defined through the casing 10 and includes an inlet 111 and an outlet 112. The inlet 111 communicates with the air vent 40 and the outlet 112. An ultraviolet LCD 30 is located in the passage 11 and powered by a power supply device 20 (FIGS. 7–10) connected to the casing 10. The power supply device 20 includes a circuit board 22 in the casing 10 and connected to the ultraviolet LCD 30. A button 12 is located on the casing 10 and is electrically connected to the power supply device 20 so that when pushing the button 12, the ultraviolet LCD 30 generates ultraviolet rays to damage germs passing through the passage 11.

The power supply device 20 includes a cable which has a plug to be connected to a cigarette lighter of the vehicle. The power supply device 20 is also be powered by batteries or other AC or DC electric currents. A fan 13 is located in the outlet 112 of the passage 11 to guide the air stream out from the outlet 112.

Figure 4:
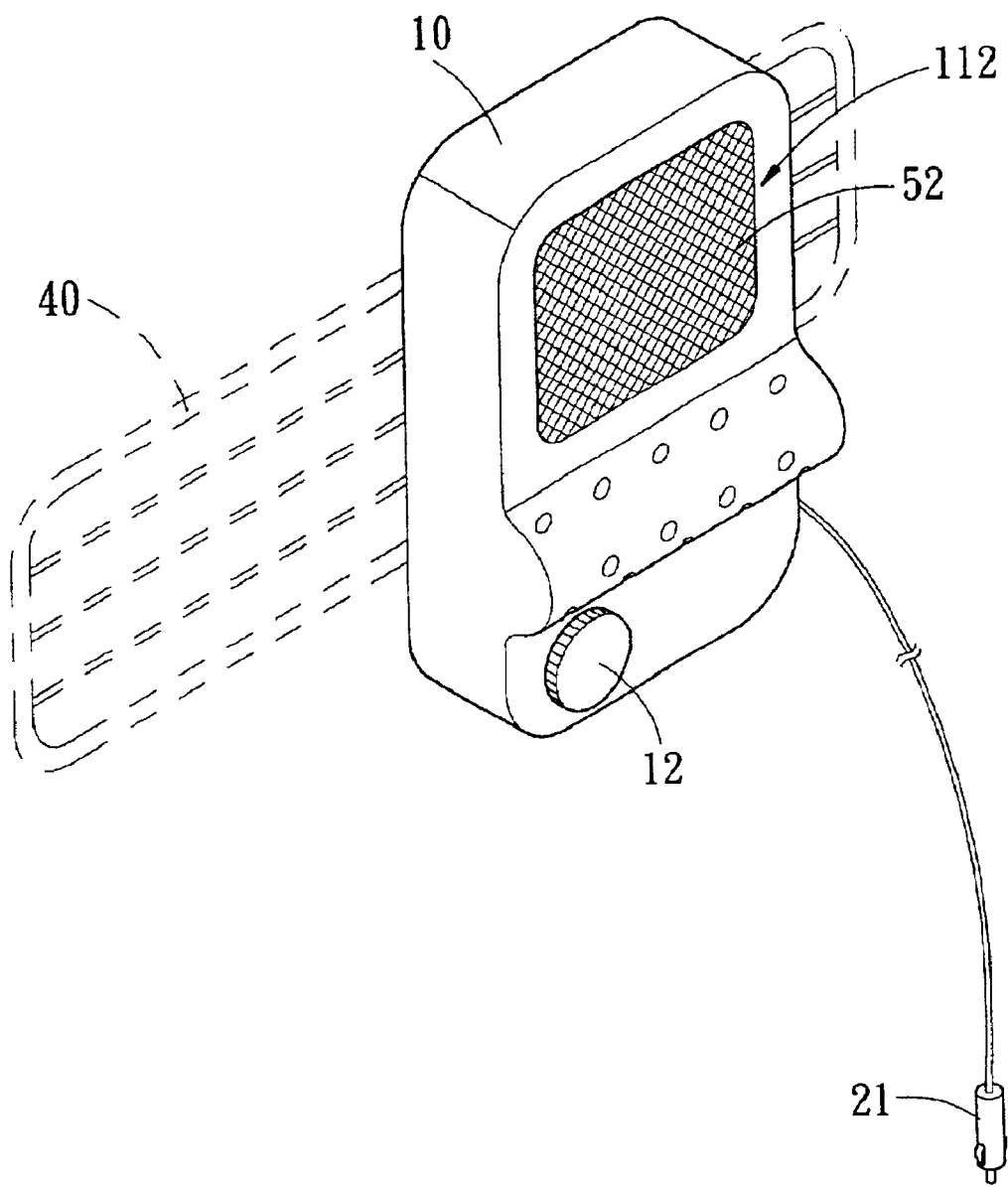
FIG. 4 shows yet another embodiment of the air sanitizing device of the present invention.

As shown in FIG. 3, a flexible tube 50 extends from the casing 10 and a light device is connected to an end of the flexible tube 50 so as to provide a lighting feature in the vehicles. The fan 13 can also be replaced with a plurality of rails 51 at the outlet 112. A filtering net 52 as shown in FIG. 4 can be engaged with the outlet 112 of the passage 11 to filter the air coming from the outlet 112. Fragrance device (not shown) can be installed in the casing 10 so as to add fragrance in the air.

Figure 6:
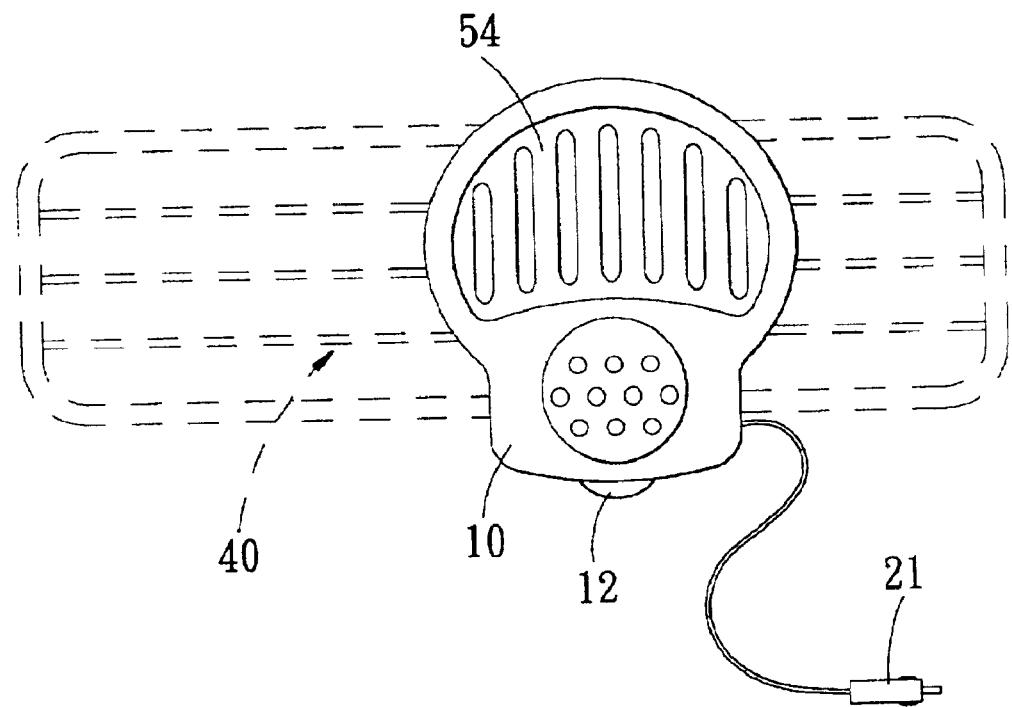
FIG. 6 shows that the fan of the air sanitizing device of the present invention is replaced with a filtering net.

An ozone generating device 53 as shown in FIG. 5 can be slidably inserted in the casing 10. FIG. 6 shows a slot panel 54 is engaged with the outlet 112.

FIG. 8 shows the circuit board 22 of the power supply device 20 includes a chip 55 which can be a #7805 current regulator chip so as to make the circuit operate in stable. A dividing resistor 56 and a limiting resistor 23 are connected to the button 12.

FIG. 9 shows that the power supply device 20 can be powered by either batteries 57 or the power from the cigarette lighter 41. A switch 58 is used to switch the two types of power supply. FIG. 10 employs two types of power supply and a chip 55 to increase the efficiency of the device.

While we have shown and described the embodiment in accordance with the present invention, it should be clear to those skilled in the art that further embodiments may be made without departing from the scope of the present invention.

What is claimed is:

1. An air sanitizing device for vehicles, comprising:
   a casing adapted to be attached to an air vent of the vehicle and having a passage including an inlet and an outlet, an ultraviolet LCD located in the passage and powered by a power supply device connected to the casing, a flexible tube extending from the casing and a light device connected to an end of the flexible tube.

2. The device as claimed in claim 1, wherein the power supply device includes a cable which is adapted to be connected to a cigarette lighter of the vehicle.

3. The device as claimed in claim 2 further comprising a button on the casing and electrically connected to the power supply device.

4. The device as claimed in claim 1 further comprising a fan located in the outlet of the passage.

5. The device as claimed in claim 1 further comprising a filtering net engaged with the outlet of the passage.

6. The device as claimed in claim 1 further comprising an ozone generating device slidably inserted in the casing.

7. The device as claimed in claim 1 further comprising a switch in the power supply device so as to shift different sources of electric power.

8. The device as claimed in claim 1 further comprising a chip in the power supply device.

* * * * *